(12) United States Patent
Rachman

(10) Patent No.: US 11,819,571 B2
(45) Date of Patent: *Nov. 21, 2023

(54) MICELLE CONSTRUCTS COMPRISING CURCUMIN

(71) Applicant: Immix Biopharma, Inc, Los Angeles, CA (US)

(72) Inventor: Ilya Rachman, Los Angeles, CA (US)

(73) Assignee: IMMIX BIOPHARMA, INC., Los Angeles, CA (US)

( * ) Notice: Subject to any disclaimer, the term of this patent is extended or adjusted under 35 U.S.C. 154(b) by 562 days.

This patent is subject to a terminal disclaimer.

(21) Appl. No.: 16/789,401

(22) Filed: Feb. 12, 2020

(65) Prior Publication Data

US 2020/0179282 A1 Jun. 11, 2020

Related U.S. Application Data

(63) Continuation of application No. 15/331,693, filed on Oct. 21, 2016, now abandoned, which is a continuation-in-part of application No. 14/385,140, filed as application No. PCT/US2013/032153 on Mar. 15, 2013, now Pat. No. 9,833,508.

(60) Provisional application No. 62/245,813, filed on Oct. 23, 2015, provisional application No. 61/701,018, filed on Sep. 14, 2012, provisional application No. 61/611,529, filed on Mar. 15, 2012.

(51) Int. Cl.
| | |
|---|---|
| A61K 9/107 | (2006.01) |
| A61K 31/12 | (2006.01) |
| A61K 31/704 | (2006.01) |
| C07K 16/28 | (2006.01) |
| A61K 45/06 | (2006.01) |
| A61K 47/68 | (2017.01) |
| A61K 9/00 | (2006.01) |
| A61K 47/24 | (2006.01) |

(52) U.S. Cl.
CPC .......... *A61K 9/1075* (2013.01); *A61K 9/0019* (2013.01); *A61K 31/12* (2013.01); *A61K 31/704* (2013.01); *A61K 45/06* (2013.01); *A61K 47/24* (2013.01); *A61K 47/6849* (2017.08); *C07K 16/28* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 8,697,098 B2 * | 4/2014 | Perumal | A61K 31/07 977/700 |
| 9,833,508 B2 | 12/2017 | Senn et al. | |
| 2013/0330412 A1 * | 12/2013 | Maitra | A61K 9/5138 424/497 |

FOREIGN PATENT DOCUMENTS

WO 2013138735 A1 9/2013

OTHER PUBLICATIONS

Tang et al (Polymer Preprints, 2009, 50:322).*
Ma et al (Journal of Biomedical Material Research, 2008, 86A:300-310).*
Lim et al (Proceedings of the 101st Annual Meeting of the American Association for Cancer Research; Apr. 17-21, 2010; Washington, DC, Philadelphia (PA):AACR; Cancer research 2010; 70(8 Suppl): Abstract nr 440).*
Gou et al (Nanoscale, 2011, 3:1558-1567).*
Abouzeid et al (J Drug Target, 2013, 21:994-1000).
Das et al (Expert Opinion on Drug Delivery, 2009, 6:285-304).
Jhaveri et al (Frontiers in Pharmacology, Apr. 2014, 5: 1-26).
Yu et al (Molecular Membrane Biology, 2010, 27:286-298).

* cited by examiner

*Primary Examiner* — Laura B Goddard
(74) *Attorney, Agent, or Firm* — Aura IP Law, PC

(57) ABSTRACT

The invention relates to the treatment of cancer. In one embodiment, the present invention provides a composition comprising a micelle construct attached to a curcumin molecule or a pharmaceutical equivalent, analog, derivative, or salt thereof, and a chemotherapy agent. In another embodiment, the present invention provides a method of treating cancer by administering a therapeutically effective amount of a composition comprising a micelle construct attached to curcumin or a pharmaceutical equivalent, analog, derivative, or salt thereof, and a chemotherapy agent.

16 Claims, 9 Drawing Sheets

MICELLE CONSTRUCTS COMPRISING CURCUMIN

RELATED APPLICATIONS

The instant application is a continuation of U.S. patent application Ser. No. 15/331,693, filed on Oct. 21, 2016, which claims the benefit of priority of U.S. patent application Ser. No. 14/385,140 filed on Sep. 12, 2014, which is a national stage of PCT/US2013/032153, filed on Mar. 15, 2013, which claims the benefit of U.S. Provisional Application Ser. No. 61/611,529 filed on Mar. 12, 2012 and U.S. Provisional Application Ser. No. 61/701,018 filed on Sep. 14, 2012, and further claims the benefit of priority of U.S. Provisional Patent Application No. 62/245,813, filed on Oct. 23, 2015. Each of these applications is incorporated by reference herein in its entirety.

BACKGROUND TO THE INVENTION

Complete and effective treatment for cancer has not been developed despite billions of dollars being spent in cancer research. Part of the reason is because tumor cells can be made up of a variety of cell types, produced as the cells proliferate and incur different mutations. This diversity, in turn, is part of what has made treatment of cancer so difficult, as a population of cancerous cells could easily include a mutant variety that happens to be resistant to any individual treatment or chemotherapy drug that is administered. The few resistant cancer cells are provided a strong selective advantage in comparison to other cells, and over time, those resistant cells increase in frequency.

Thus, there is a need in the art for the development of additional cancer treatments, including those that have the ability to better target drug resistant tumors and potentially bypass the diversity of cancer cells.

SUMMARY OF INVENTION

Various embodiments include a method of treating cancer in a subject, comprising providing a composition comprising a micelle construct attached to an inhibitor of NF-kB, and administering a therapeutically effective dosage of the composition to the subject. In one embodiment, the micelle construct is targeted. In another embodiment, the micelle construct is targeted to bind to glut-1. In another embodiment, the micelle construct is less than 30 nm. In another embodiment, the inhibitor of NF-kB is curcumin, or a pharmaceutical equivalent, analog, derivative, and/or salt thereof. In another embodiment, the inhibitor of NF-kB is an siRNA molecule. In another embodiment, the composition further comprises one or more chemotherapy agents. In another embodiment, the micelle construct is further attached to one or more dox molecules. In another embodiment, the subject is a human. In another embodiment, the subject is a mouse. In another embodiment, the cancer is colon cancer. In another embodiment, the cancer is breast cancer.

Other embodiments include a pharmaceutical composition, comprising an inhibitor of NF-kB, a glut-1 antibody, and a pharmaceutically acceptable carrier. In another embodiment, the inhibitor of NF-kB is an siRNA molecule. In another embodiment, the glut-I antibody is toxic. In another embodiment, the inhibitor of NF-kB is therapeutically effective amount of a compound of the formula:

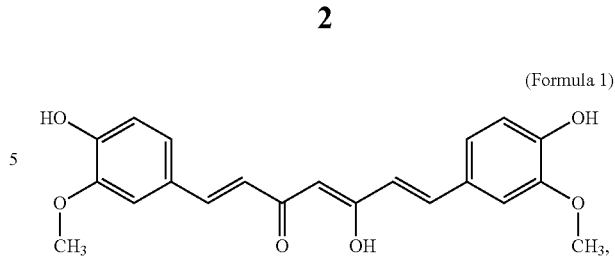

(Formula 1)

or a pharmaceutical equivalent, analog, derivative, and/or salt thereof. In another embodiment, the inhibitor of NF-kB is therapeutically effective amount of a compound of the formula:

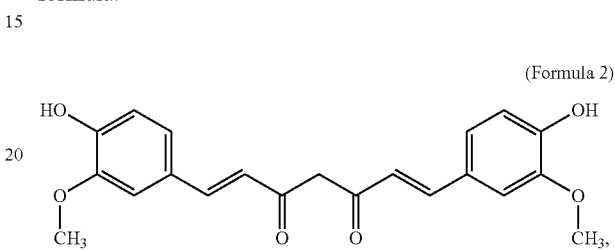

(Formula 2)

or a pharmaceutical equivalent, analog, derivative, and/or salt thereof. In another embodiment, the composition further comprises a micelle.

Other embodiments include a method of inhibiting cell growth of a tumor cell, comprising providing a composition comprising an antibody targeting Glut-1 and an inhibitor of NF-kB, wherein the antibody targeting Glut-1 and the inhibitor of NF-kB are conjugated to one another, and inhibiting cell growth by administering a therapeutically effective dosage to the tumor cell. In another embodiment, the inhibitor of NF-kB comprises siRNA. In another embodiment, the inhibitor of NF-kB comprises curcumin. In another embodiment, the inhibitor is at a concentration above 8.3 ug/ml. In another embodiment, the antibody targeting glut-1 is toxic. In another embodiment, the antibody targeting glut-1 is at a concentration above 31.7 ug/ml. In another embodiment, the tumor cell is a breast cancer and/or colon cancer cell type. In another embodiment, the composition further comprises a micelle.

Various embodiments include a nanoconjugate, comprising a targeting module for a mammalian glucose transporter, and an inhibitor of an inflammatory pathway mediator, where the targeting module for a mammalian glucose transporter and the inhibitor of an inflammatory pathway mediator are conjugated to one another. In another embodiment, the inflammatory pathway mediator comprises NF-kB. In another embodiment, the mammalian glucose transporter is a glut-1 receptor. In another embodiment, the nanoconjugate is between 20 nm and 50 nm. In another embodiment, the nanoconjugate is less than 60 nm. In another embodiment, the nanoconjugate is less than 20 nm. In another embodiment, the nanoconjugate is enclosed by a micelle.

In one embodiment, disclosed herein are compositions, comprising, a micelle construct; an antibody single chain fragment variable (scFv); a NF-kb inhibitor; and a topoisomerase II inhibitor. In one embodiment, the scFv is conjugated to the micelle construct. In one embodiment, the micelle construct is conjugated to the NF-kb inhibitor. In one embodiment, the micelle construct is conjugated to the NF-kb inhibitor and the topoisomerase II inhibitor. In one embodiment, the NF-kb inhibitor is curcumin or a pharmaceutical equivalent, analog, derivative, and/or salt thereof. In one embodiment, the topoisomerase II inhibitor is dox or a pharmaceutical equivalent, analog, derivative, and/or salt thereof. In one embodiment, the scFv is a glut-1_1 or glut-1_2 scFv. In one embodiment, the micelle construct is targeted to bind to glut-1_1 and/or glut-1_2 scFv. In one embodiment, the composition forms a targeted micelle. In one embodiment, the molecular size of the targeted micelle is 30 nm or less. In one embodiment, the composition further comprises a pharmaceutically acceptable carrier.

In another embodiment, disclosed herein are methods of delivering a drug molecule to a tumor site of a subject comprising: attaching the drug molecule to a targeted micelle, wherein the targeted micelle comprises a micelle construct and an antibody single chain fragment variable (scFv); and delivering the drug molecule attached to the targeted micelle to the tumor site through intracellular delivery. In one embodiment, the drug molecule comprises dox and/or curcumin or a pharmaceutical equivalent, analog, derivative, and/or salt thereof. In one embodiment, the molecular size of the micelle is 30 nm or less. In one embodiment, the tumor is a doxorubicin-resistant tumor. In one embodiment, the subject is human.

In another embodiment, disclosed herein are methods of treating cancer comprising administering to a subject in need thereof, a therapeutically effective dosage of a composition comprising a micelle construct, an antibody single chain fragment variable (scFv), a NF-kb inhibitor, and a topoisomerase II inhibitor. In one embodiment, the composition is administered to the subject intravenously. In one embodiment, the subject is human. In one embodiment, the cancer is brain cancer. In one embodiment, the cancer is ovarian cancer. In one embodiment, the cancer is colon cancer. In one embodiment, the cancer is a doxorubicin-resistant cancer. In one embodiment, the molecular size of the targeted micelle is 30 nm or less.

In another embodiment, disclosed herein are methods of inhibiting cell growth of a tumor cell, comprising: providing a composition comprising a micelle construct, an antibody single chain fragment variable (scFv), a NF-kb inhibitor and a topoisomerase II inhibitor; and inhibiting cell growth by administering a therapeutically effective dosage of the composition to the tumor cell. In one embodiment, the topoisomerase inhibitor comprises Dox. In one embodiment, the NF-kB inhibitor comprises curcumin. In one embodiment, the tumor cell is a brain cancer cell, a ovarian cancer cell, and/or colon cancer cell.

In another embodiment, disclosed herein are nanoconjugates comprising: a micelle construct; an antibody single chain fragment variable (scFv); a NF-kb inhibitor; and a topoisomerase II inhibitor; and wherein the micelle construct, the antibody single chain fragment variable (scFv), the NF-kb inhibitor, and the topoisomerase II inhibitor are conjugated to one another. In one embodiment, the nanoconjugate has a molecular size between 20 nm and 50 nm. In one embodiment, the nanoconjugate has a molecular size between 10 nm and 20 nm. In one embodiment, the nanoconjugate has a molecular size of less than 20 nm. In one embodiment, the nanoconjugate is enclosed by a micelle.

BRIEF DESCRIPTION OF THE DRAWINGS

Exemplary embodiments are illustrated in referenced figures. It is intended that the embodiments and figures disclosed herein are to be considered illustrative rather than restrictive.

DESCRIPTION OF THE INVENTION

Figure 1:
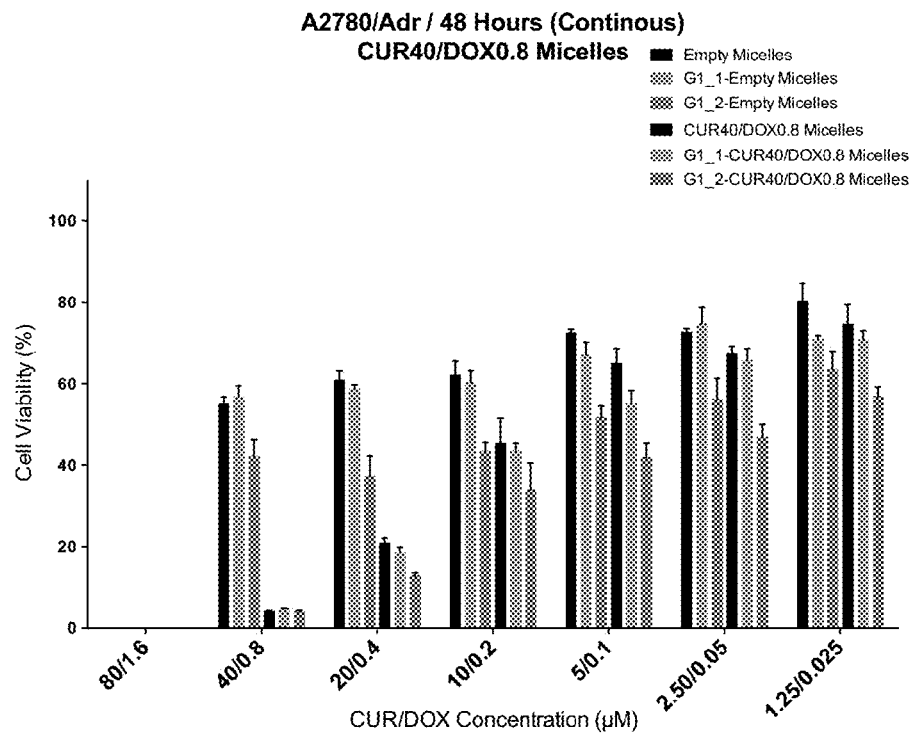
FIG. 1 depicts, in accordance with the embodiments herein, the efficacy of CUR40/DOX0.8 micelles on Doxorubicin-resistant ovarian carcinoma cell lines, A2780/Adr, after 48 hours of continuous contact. The columns show the cell viability at CUR/DOX concentrations 80/1.6, 40/0.8, 20/0.4, 10/0.2, 5/0.1, 2.5/0.05, 1.25/0.025. Experimental data compares the cell viability of EmptyMicelles, G1_1-EmptyMicelles, G1_2-EmptyMicelles, CUR40/DOX0.8 Micelles, G1_1-CUR40/DOX0.8 Micelles, and G1_2-CUR40/DOX0.8 micelles.

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, NY 2001); March, Advanced Organic Chemistry Reactions, Mechanisms and Structure 7th ed., J. Wiley & Sons (New York, NY 2013); and Sambrook and Russel, Molecular Cloning: A Laboratory Manual 4th ed., Cold Spring Harbor Laboratory Press (Cold Spring Harbor, NY 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

The term "nanoconjugate" may also include liposomal and micelle constructs.

As used herein, "MDA-MB-231" refers to a breast tumor cell line.

As used herein, "HCT-116" refers to a colon tumor cell line. As used herein, "A2780" refers to an ovarian cancer cell line. As used herein, "U87MG" or "U87" refers to a brain cancer cell line.

As used herein, the abbreviation of "CUR" refers to curcumin. As used herein, the term "DOX" refers to doxorubicin.

As used herein, the terms "glut-1," "GLUT-1," "G1," or "glut1," used interchangeably, refers to a glucose transporter antibody. The term scFv, as used herein, refers to single chain variable fragment. Thus, the terms GLUT-1_1 and/or GLUT1_2 scFv refers to a single chain variable fragment of the GLUT-1 antibody.

As described herein, the inventor has recognized that effective cancer treatment would benefit from attacking the cancer early, as well as attacking aggressively. This could come in the form of administering a combination of drugs for treatment, as the odds of a single cell being resistant to a larger quantity of drugs are lower. Additionally, an effective cancer treatment could also potentially bypass the diversity of cancer cells by targeting processes that cancer cells rely on for their very growth. One such process is tumors' reliance on producing and processing sugar for its cell growth.

As described herein, the inventor has developed various compositions and methods for the treatment of cancers and associated conditions. In accordance with embodiments further described herein, the inventor developed and optimized cancer therapeutic compositions and methods for effective delivery and minimized toxicity. For example, in one embodiment, utilizing a single chain antibody allows a more efficient delivery in conjunction with various embodiments herein. In accordance with various embodiments further disclosed herein, the inventor also attached curcumin to a targeted micelle. By attaching curcumin to a targeted micelle, treatment was administered at a significantly lower dosage, thus reducing toxicity while effectively inhibiting tumor growth. As compared to the liposomal forms of both doxorubicin and curcumin, a micellar preparation is of significantly smaller molecular size (10-20 nm vs. 80-150 nm liposomes) resulting in improved tumor mass penetration from the vascular bed, thus creating a more effective cancer therapeutic.

As readily apparent to one of skill in the art, various materials and methods are readily available and known to obtain curcumin and attach curcumin molecules to a construct or nanoconjugate in accordance with various embodiments herein. An example of curcumin may be a compound of the following formula:

(Formula 1)

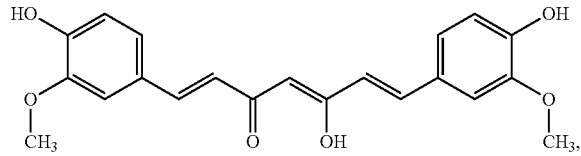 [SMILES: COc1cc(/C=C/C(=O)/C=C(O)/C=C/c2ccc(O)c(OC)c2)ccc1O]

or a pharmaceutical equivalent, analog, derivative, and/or salt thereof.

In accordance with embodiments described herein, the inventors prepared various micelle compounds as cancer therapeutics. In one embodiment, the inventors prepared a cancer therapeutic construct based on a nano-sized lipid carrier encapsulating a cell-toxic chemotherapy molecule combined with an inhibitor of tumor chemo-resistance, targeted to tumor cells by tumor-recognizing antibody on its surface. Studies using chemotherapy-resistant colon and breast cancer lines in-vitro and in mouse xenografts showed significant tumor growth suppression, with almost no tumor growth seen (as compared to over 300% increase in tumor volume in control animals). Additionally, the construct was developed to be of optimal molecular size and biophysical properties in order to deliver clinically meaningful drug quantities in a whole animal setting, while avoiding toxicity associated with intravenous chemotherapy treatment.

In one embodiment, the effects of various components of therapeutic constructs were examined as follows: Mice were implanted subcutaneously with HCT-116 colon adenocarcinoma cells, and those in whom tumor mass volume reached 250 mm$^3$ were included. The animals with the implanted tumors were divided into six (6) groups (with 6 mice per group) and treated with one of the following:
1) Phosphate Buffered Saline (Control group)—(PBS Control)
2) Anti-Glut1 Antibody (Ab) linked to empty micelle-(Glut1-Empty Micelles)
3) Micelles containing Curcumin at a dose of 4 mg/kg—(Cur Micelles)
4) Anti-Glut I Ab linked to Curcumin-containing micelles—(Glut1-Cur Micelles)
5) Micelles containing Doxorubicin (0.4 mg/kg) and Curcumin—(Cur+Dox Micelles)
6) The complete compound, Anti-Glut I Ab linked to micelles containing Doxorubicin (0.4 mg/kg) and Curcumin—Glut1-Cur+Dox Micelles.

As further disclosed herein, each group of mice was given 7 total intravenous injections every other day starting on Day 0. The tumor volume in each group of animals was measured on Day 12. Results were as follows:
1) The control group, treated with PBS only, showed a 180% increase in tumor volume on Day 12 as compared with Day 0
2) Glut I-Empty Micelles group showed a 100% increase in tumor volume
3) Cur Micelles group showed a 140% increase in tumor volume
4) Glut1-Cur Micelles group showed a 46% increase in tumor volume size
5) Cur+Dox Micelles group showed a 86% increase in tumor volume and
6) Glut1-Cur+Dox Micelles group showed just 6% increase in tumor volume.

The tumor inhibitory effects of various components were additive, with the complete compound showing the most dramatic, almost complete, inhibition of tumor growth at Day 12 time point. Importantly, the tumor inhibitory effect grew in size as each additional component was being added to the experimental construct. The inventors also demonstrated that the combination of anti-Glut1 Ab and curcumin-loaded micelles was the second most potent formulation in tumor growth suppression. Cur+Dox micelles and Glut IA-linked empty micelles showed similar tumor suppressing effect, at approximately ½ of the effect of the complete compound. The effect on tumor growth suppression observed in vivo paralleled very closely results obtained from additional in vitro studies by the inventors described herein. Specifically, the same additive effects of various compound components on tumor growth suppression were seen in vitro.

In one embodiment, the present invention provides a method of treating cancer and/or inhibiting growth in a tumor cell in a subject, by providing a composition comprising a micelle targeted by glut-1 receptor antibody and attached to curcumin and/or dox, and administering a therapeutically effective dosage to the subject. In another embodiment, the composition is administered to the subject intravenously.

In accordance with embodiments further described herein, by utilizing dox attached to a targeted micelle as a lipid-based delivery vehicle, rather than liposomal dox, or just dox, for example, the inventors created a cancer treatment with significantly high penetration of tumor mass. In addition to creating high tumor mass penetration, administering a composition comprising a dox attached to a targeted micelle optimized intracellular delivery of dox within the tumor cell itself. Because dox acts as a weakly basic compound, if it enters a low pH environment, or the lysosome of a tumor cell for example, the dox can lose much of its effectiveness for inhibiting tumor cell growth. By administering dox attached to a targeted micelle, rather than administering liposomal dox for example, the inventors enabled the dox to instead enter the cytoplasm, thus optimizing intracellular delivery. Additionally, dox can have high toxicity which can thus limit its practical application in vivo and usefulness as a cancer treatment for human subjects. In contrast, the inventors administered dox attached to a targeted micelle, resulting in further optimization of its effectiveness as a cancer therapeutic.

In accordance with various embodiments further disclosed herein, the inventors also attached curcumin to a targeted micelle. Due to its nonsoluble properties, if administered directly, curcumin must be administered at high concentrations to be effective inhibiting tumor growth. However, at those same high concentrations, curcumin results in high toxicity, thus making it an impractical and ineffective cancer treatment in vivo, and particularly difficult for use in human patients. In accordance with an embodiment herein, by attaching curcumin to a targeted micelle, treatment can be administered at a significantly lower dosage, thus reducing toxicity while effectively inhibiting tumor growth.

As compared to the liposomal forms of both doxorubicin and curcumin, a micellar preparation is of significantly smaller molecular size (10-20 nm vs. 80-150 nm liposomes) resulting in improved tumor mass penetration from the vascular bed, thus creating a more effective cancer therapeutic. Additionally, in accordance with an embodiment herein, the addition of the Glut-1 Ab to the micelle greatly increased its therapeutic efficacy over the un-targeted micelle preparations through improved intracellular delivery of its contents. Glut-1 presents an attractive extracellular target since it is one of the main glucose transporters involved in tumor glucose uptake. Solid tumors can take up glucose at much higher rates than do normal cells. Glycolysis represents a main source of energy and carbon building blocks for growing tumors. Thus, in accordance with an embodiment herein, a micelle construct with a Glut-1 Ab is an effective cancer therapeutic, as glut-1 overexpression will persist even in the face of tumor phenotypic evolution, and it will be difficult for tumors to mutate away from glut-1 overexpression and still retain their high growth potential. In regard to using glut-1 as the tumor targeting entity, by binding to the tumor membrane-overexpressed glut-1, various embodiments of therapeutic micelles described herein get endocytosed into the cytoplasm rather than the low-pH lysosome, thereby increasing the therapeutic efficacy of doxorubicin (which has much lower activity at low pH).

Since the tumor lines used in these experiments were doxorubicin-resistant, it was critical that curcumin delivery occurred contemporaneously with doxorubicin exposure in order for it to exert its tumoricidal effect. As NF-kappa B overexpression and its attendant apoptosis- and chemotherapy-resistance are present in advanced cancers, the inventors designed various embodiments herein to include an NF-kappa B inhibitor (for example, curcumin) in order to unlock the cidal effect of doxorubicin. In one embodiment, the present invention is a tumor-targeted micelle containing a tumor-cidal agent coupled with an apoptosis inhibitor with significant in vivo tumor inhibitory effect and clear applicability to human cancer therapeutics.

As disclosed herein, the inventors also administered compositions comprising both (I) siRNA inhibitors of NF-kB, and (2) antibody targeting glut-1 receptors, to both HCT-116 cells and MDA-MB-23 J cells (i.e. colon tumor cells, and breast tumor cells, respectively), and examined the effects of the composition on cell viability as compared to normal cell type growth. Using MTI viability assays, higher dosages of composition comprising siRNA inhibitor of NF-kB, and antibody targeting glut-1 receptors (31.7 ug/ml glut-l Ab, and 8.3 ug/ml NF-kB siRNA) resulted in a decrease in % of cell viability as compared to non-treated cells.

As further disclosed herein, the inventors prepared compositions comprising nanoconjugates (or conjugates) made up of polymeric micelles and one or more antibodies targeting glut-l conjugated to one or more curcumin molecules. The compositions were administered to both HCT-116 cells and MDA-MB-231 cells (i.e. colon tumor cells, and breast tumor cells, respectively), with and without DOX, and examined the effects of the composition on cell viability as compared to normal cell type growth. The result demonstrated that the addition of the glut-l antibody onto curcumin micelles, in the presence of DOX in the system, produces significant enhancement to the toxicity and demonstrated that the combination treatment is more effective than if applied in isolation.

In one embodiment, the present invention provides a method of treating a cancer in an individual by administering a therapeutically effective dosage of a composition comprising an inhibitor of an inflammatory pathway and/or a glut antibody to the individual. In another embodiment, the inhibitor of an inflammatory pathway is an inhibitor of NF-kB. In another embodiment, the administration of the composition increases efficacy of additional cancer therapeutics administered to the individual. In another embodiment, the additional cancer therapeutics includes DOX. In another embodiment, the glut antibody is an antibody targeting glut-1. In another embodiment, one or more chemotherapy agents may be added to the composition. In another embodiment, the inhibitor of NF-kB and glut antibody form a nanoconjugate. In another embodiment, the nanoconjugate is delivered as part of a micelle. In another embodiment, the construct further comprises one or more chemotherapy agents. In another embodiment, the nanoconjugate is used as a chemosensitizer prior to chemotherapy. In another embodiment, the individual is a mammal. In another embodiment, the individual is a rodent. In another embodiment, the individual is human. In another embodiment, the inhibitor of NF-kB is one or more siRNA molecules. In another embodiment, the inhibitor of NF-kB is one or more molecules of curcumin. In another embodiment, the glut-1 antibody is toxic to the target. In another embodiment, the cancer is colon cancer. In another embodiment, the cancer is breast cancer. In another embodiment, the cancer is brain cancer. In another embodiment, the tumor is a HCT-116 and/or MDA-MB-231 cell. In another embodiment, the inhibitor of NF-kB is administered at about 8.3 ug/ml. In another embodiment, the inhibitor of NF-kB is administered at more than 8.3 ug/ml. In another embodiment, the glut-I antibody is administered at about 31.7 ug/ml. In another embodiment, the glut-J antibody is administered at more than 31.7 ug/ml. In another embodiment, the composition is administered to the individual by direct injection.

In another embodiment, the present invention provides a method of decreasing the size of a tumor by administering a therapeutically effective dosage of a composition comprising an inhibitor of NF-kB and/or a glut-1 antibody to the tumor. In another embodiment, the inhibitor of NF-kB is an siRNA molecule. In another embodiment, the glut-1 antibody is toxic to the tumor. In another embodiment, the tumor is a colon tumor. In another embodiment, the tumor is a breast tumor. In another embodiment, the tumor is in the brain. In another embodiment, the tumor is a HCT-116 and/or MDA-MB-231 cell. In another embodiment, the inhibitor of NF-kB is administered at about 8.3 ug/ml. In another embodiment, the inhibitor of NF-kB is administered at more than 8.3 ug/ml. In another embodiment, the glut-1 antibody is administered at about 31.7 ug/ml. In another embodiment, the glut-1 antibody is administered at more than 31.7 ug/ml.

In another embodiment, the present invention provides a nanoconjugate construct made up of one or more targeting segments, linker segments, and/or NF-kB inhibitors. In another embodiment, the one or more NF-kB inhibitors is made up of curcumin. In another embodiment, the one or more targeting segments is an antibody targeting glut-1.

As readily apparent to one of skill in the art, nanoconjugates and other nanomedicines for cancer treatment benefit from a small size. Vessels that supply tumors often leak and can block delivery of candidate treatments to the tumor. Similarly, nanoconjugates that are too large cannot penetrate tissue. Thus, in accordance with various embodiments described herein, an antibody targeting Glut-1 conjugated to one or more inhibitors of NF-kB, such as curcumin, provides benefits of high efficacy due to a size less than 40 nm. In one embodiment, the nanoconjugate is less than 20 nm. In another embodiment, the nanoconjugate is between 20 nm and 40 nm. In another embodiment, the nanoconjugate is between 20 nm and 60 nm. In another embodiment, the nanoconjugate is between 60 nm and 100 nm.

In various embodiments, the present invention provides pharmaceutical compositions including a pharmaceutically acceptable excipient along with a therapeutically effective amount of composition comprising an inhibitor of Nf-kB and an antibody targeting glut-1. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The*

*Science and Practice of Pharmacy* (Gennaro ed. 20th edition, Williams & Wilkins PA, USA) (2000).

Typical dosages of an effective composition comprising siRNA encoding Nf-kB and Ab targeting glut-1 or conjugates of curcumin and one or more antibodies targeting glut-1 can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

The present invention is also directed to a kit to preparation of and use of a composition comprising one or more inhibitors of Nf-kB and one or more antibodies targeting glut-1. The kit is useful for practicing the inventive method of treating cancer or tumors. The kit is an assemblage of materials or components, including at least one of the inventive compositions.

The exact nature of the components configured in the inventive kit depends on its intended purpose. For example, some embodiments are configured for the purpose of treating a tumor and/or cancer, such as colon or breast cancer. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to decrease or kill a tumor. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

In one embodiment, disclosed herein are compositions comprising a micelle construct; an antibody single chain fragment variable (scFv); a NF-kb inhibitor; and a topoisomerase II inhibitor. In one embodiment, the scFv is conjugated to the micelle construct. In one embodiment, the micelle construct is conjugated to the NF-kb inhibitor. In one embodiment, the micelle construct is conjugated to the NF-kb inhibitor and the topoisomerase II inhibitor. In one embodiment, the NF-kb inhibitor is curcumin or a pharmaceutical equivalent, analog, derivative, and/or salt thereof. In one embodiment, the topoisomerase II inhibitor is dox or a pharmaceutical equivalent, analog, derivative, and/or salt thereof. In one embodiment, the scFv is a glut-1_1 or glut-1_2 scFv. In one embodiment, the micelle construct is targeted to bind to glut-1_1 and/or glut-1_2 scFv. In one embodiment, the composition forms a targeted micelle. In one embodiment, the molecular size of the targeted micelle is 30 nm or less. In one embodiment, the composition further comprises a pharmaceutically acceptable carrier.

In another embodiment, disclosed herein are methods of delivering a drug molecule to a tumor site of a subject comprising: attaching the drug molecule to a targeted micelle, wherein the targeted micelle comprises a micelle construct and an antibody single chain fragment variable (scFv); and delivering the drug molecule attached to the targeted micelle to the tumor site through intracellular delivery. In one embodiment, the drug molecule comprises dox and/or curcumin or a pharmaceutical equivalent, analog, derivative, and/or salt thereof. In one embodiment, the molecular size of the micelle is 30 nm or less. In one embodiment, the tumor is a doxorubicin-resistant tumor. In one embodiment, the subject is human.

In another embodiment, disclosed herein are methods of treating cancer comprising administering to a subject in need thereof, a therapeutically effective dosage of a composition comprising a micelle construct, an antibody single chain fragment variable (scFv), a NF-kb inhibitor, and a topoisomerase II inhibitor. In one embodiment, the composition is administered to the subject intravenously. In one embodiment, the subject is human. In one embodiment, the cancer is brain cancer. In one embodiment, the cancer is ovarian cancer. In one embodiment, the cancer is colon cancer. In one embodiment, the cancer is a doxorubicin-resistant cancer. In one embodiment, the molecular size of the targeted micelle is 30 nm or less.

In another embodiment, disclosed herein are methods of inhibiting cell growth of a tumor cell, comprising: providing a composition comprising a micelle construct, an antibody single chain fragment variable (scFv), a NF-kb inhibitor and a topoisomerase II inhibitor; and inhibiting cell growth by administering a therapeutically effective dosage of the composition to the tumor cell. In one embodiment, the topoisomerase inhibitor comprises Dox. In one embodiment, the NF-kB inhibitor comprises curcumin. In one embodiment, the tumor cell is a brain cancer cell, a ovarian cancer cell, and/or colon cancer cell.

In another embodiment, disclosed herein are nanoconjugates comprising: a micelle construct; an antibody single chain fragment variable (scFv); a NF-kb inhibitor; and a topoisomerase II inhibitor; and wherein the micelle construct, the antibody single chain fragment variable (scFv), the NF-kb inhibitor, and the topoisomerase II inhibitor are conjugated to one another. In one embodiment, the nanoconjugate is between 20 nm and 50 nm. In one embodiment, the nanoconjugate is between 10 nm and 20 nm. In one embodiment, the nanoconjugate is less than 20 nm. In one embodiment, the nanoconjugate is enclosed by a micelle.

Figure 17:
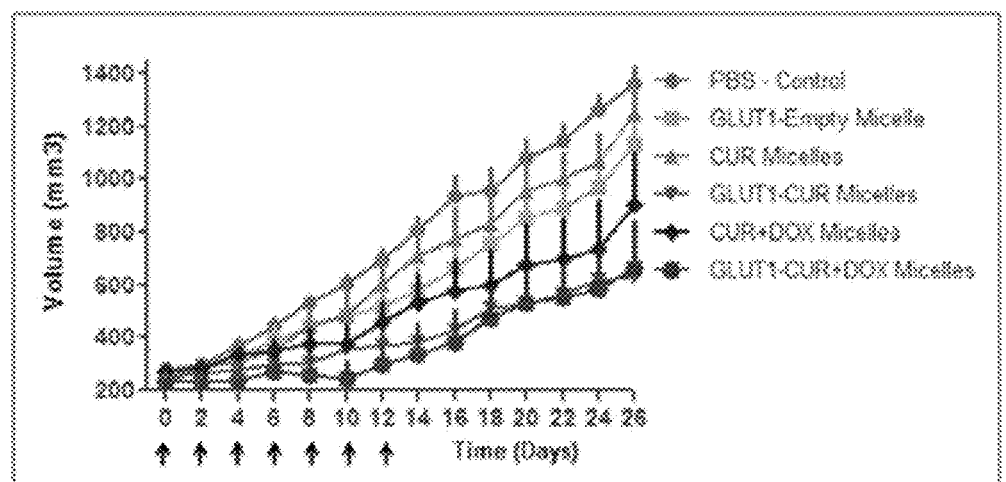
FIG. 17 depicts, in accordance with the embodiments herein, a chart of an in vivo study of Glut1-CUR+DOX constructs using HCT-116 cell line. Nude mice bearing ~250 mm$^3$ HCT-116 tumors were treated every 2 days starting at Day 0 (7 total IV injections) at a dose of 4 mg/kg CUR and 0.4 mg/kg DOX. N=6 with SEM. As the figure demonstrates, the tumor inhibitory effects of various components were clearly additive, with the complete compound showing the most dramatic, almost compete, inhibition of tumor growth at Day 12 time point. Additionally, each additional component results in an additive, synergistic effect resulting in further tumor shrinkage with the addition of each component.
Figure 18:
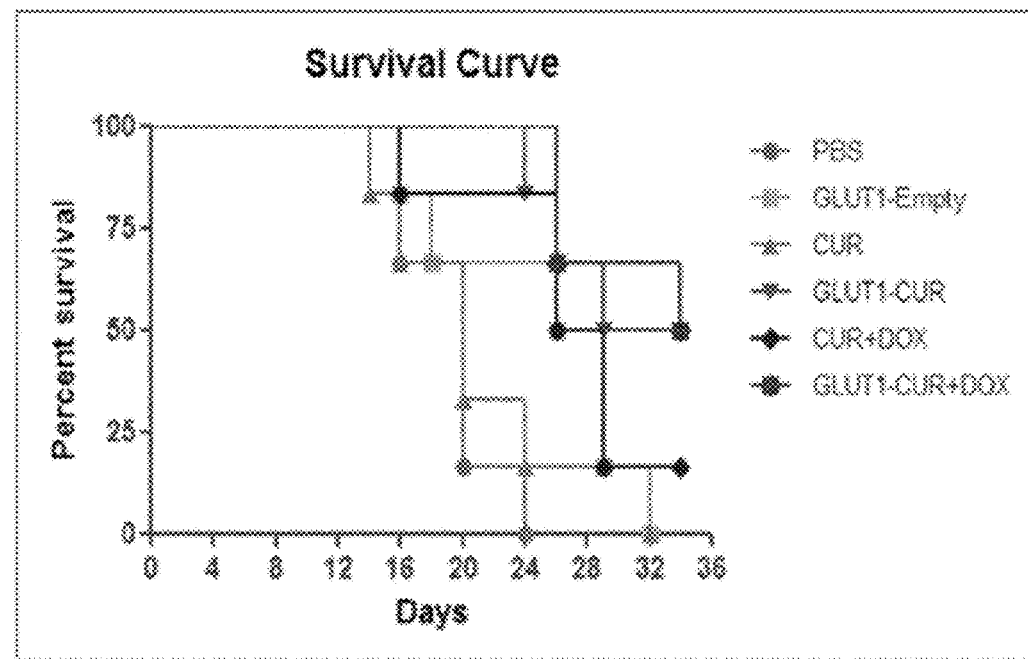
FIG. 18 depicts, in accordance with the embodiments herein, a survivor curve chart of the in-vivo study of Glut1-CUR+DOX constructs using HCT-116 cell lines described in FIG. 17 and herein. Nude mice bearing ~250 mm$^3$ HCT-116 tumors were treated every 2 days starting at Day 0 (7 total IV injections) at a dose of 4 mg/kg CUR and 0.4 mg/kg DOX. N=6 with SEM. Survival was determined when the tumor reached 1000 mm$^3$. One way ANOVA with Tukey's post test showed that GLUT1-CUR and GLUT1-CUR+DOX were significantly different from PBS control group. Also, GLUT1-CUR+DOX was significantly different from the CUR group. ($p<0.05$). Two way ANOVA resulted in the following ($p<0.05$): PBS is significantly different from: GLUT1-CUR beginning at day 14, CUR+DOX at day 20, and GLUT1-CUR+DOX at day 12 till the end of the study. GLUT1-Empty is significantly different from: GLUT1-CUR beginning at day 20, and GLUT1-CUR+DOX at day 14 till the end of the study. As the figure demonstrates, the tumor inhibitory effects of various components were clearly additive, with the complete compound showing the most dramatic, almost compete, inhibition of tumor growth at Day 12 time point. Additionally, each additional component results in an additive, synergistic effect resulting in further tumor shrinkage with the addition of each component.

In one embodiment, as demonstrated in FIGS. 17 and 18, the tumor inhibitory effects of various components were clearly additive, with the complete compound showing the most dramatic, almost compete, inhibition of tumor growth at Day 12 time point. Additionally, each additional component resulted in an additive, synergistic effect resulting in further tumor shrinkage with the addition of each component.

Embodiments of the present disclosure are further described in the following examples. The examples are merely illustrative and do not in any way limit the scope of the invention as claimed.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

Similarly, the various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "'about." Accordingly, in some embodiments, the numerical parameters set forth in the written description and attached claims are approximations that can vary depending upon the desired properties sought to be obtained by a particular embodiment.

In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "'an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

Example 1: Materials 1,2-Distearoyl-sn-glycero-3-phosphoethanolamine-N-[methoxy (polyethylene glycol)-2000] (PEG-PE) was from Avanti Polar Lipids (Alabaster, AL, USA). pNP-PEG$_{3400}$-pNP was purchased from Laysan Bio (Arab, AL). Curcumin (CUR), vitamin E and triethylamine (TEA) were purchased from Sigma (St. Louis, MO, USA). Doxorubicin HCl (DOX) was from LC Laboratories (Woburn, MA). Accumax was from Innovative Cell Technologies, Inc. (San Diego, CA). The CellTiter-Glo luminescent cell viability assay kit was from Promega (Fitchburg, WI). All other reagents were of analytical grade. DOX free base was obtained by incubating DOX HCl (in methanol, 0.5 mg/ml) with 5-fold molar excess of TEA overnight. pNP-PEG$_{3400}$-PE was synthesized in-house.

Example 2: Micelle Preparation

DOX and/or CUR drug-loaded mixed micelles were prepared by the thin film hydration method. CUR (1 mg/ml in 0.1% acetic acid-methanol solution) and/or DOX free base (0.5 mg/ml in methanol solution) were added to PEG$_{2000}$-PE solution in chloroform. Initial drug amounts were adjusted after the formulation optimization studies to result in CUR:DOX ratio of 32 (w/w). The organic solvents were removed by the rotary evaporation and a thin film of drugs/micelle-forming material mixture was formed. This film was further dried overnight in freeze-dryer to remove any residuals of organic solvents (Freezone 4.5 Freeze Dry System, Labconco, Kansas City, MO). Drug-loaded micelles were formed by resuspending the film in phosphate buffered saline (PBS) pH 7.2, to give the final concentration of micelle forming materials of 5 mM in all formulations. The micelle formulations were dialyzed 1 h against PBS pH 7.2 to remove excess of TEA. Excess non-incorporated drugs were separated by filtration through a 0.2 μm syringe filter.

To obtain targeted micelles, GLUT-1 scFv was reacted with pNP-PEG$_{3400}$-PE. Briefly, required amount of pNP-PEG$_{3400}$-PE in chloroform was added into the round bottom flask and polymer film was formed after removing the solvent by rotary evaporation followed by drying under vacuum. The film was hydrated and vortexed first with citrate-buffered saline (CBS) pH 5.0 to prevent early hydrolysis of pNP distal groups. After forming micelles, GLUT-1 scFv solution in PBS (pH 7.4) was added to the mixture, and the pH was adjusted to 8.2 with NaOH. Molar ratio of pNP groups to scFv was kept at 40:1. Reaction time was overnight at 4° C. to allow sufficient conjugation and the complete hydrolysis of the unreacted pNP groups at the higher pH. Targeted-micelles were then dialyzed using a 50,000 MWCO cellulose ester membrane against PBS (pH 7.4) for 4 hours at 4° C. to ensure the complete removal of the unconjugated scFv. Conjugation efficiency of GLUT-1 scFv was measured using a micro BCA kit (Pierce, Rockford, IL) according to the manufacturer's instructions. GLUT-1 scFv conjugated micelles were mixed and co-incubated with drug loaded PEG-PE micelles for 4 hours at room temperature. The final GLUT-1 scFv mol ratio in the micelles was adjusted to 0.05%.

Example 3: GLUT-1 scFv Modified Micelle Cytotoxicity on Ovarian Cancer Cell Line For cytotoxicity evaluations, A2780 human ovarian carcinoma (ATCC) and its Doxorubicin resistant derivative A2780/Adr (ECACC) were used. A2780 cells were cultured in RPMI medium supplemented with 10% FBS and 1% penicillin-streptomycin. Drug resistant ovarian cancer cells were grown in same medium with the addition of 100 nM DOX.

The cells were seeded in 96-well plates at a density of 3000 cells/well or 5,000 cells/well for 48 or 24 hours treatment groups, respectively. The cells were treated with free drugs or micelle formulations containing 40 μM CUR and 0.8 μM DOX in serum complete RPMI medium. The cells were incubated 24 h and 48 h continuously in the continuous treatment groups. Additionally, in another treatment regimen the cells were incubated with drugs/micelles for 4 hours then washed and further incubated for 44 h. At the end of treatment times, the wells were washed twice with medium and then incubated with 50 μl medium containing 20% (v/v) CellTiter-Blue reagent. The fluorescent emission values were measured and % cell viability was calculated by using PBS treated cells as the control group.

Example 4: 3D Glioblastoma Spheroids Preparation and Cytotoxicity Evaluation of Micelles The U87MG cells were cultured in DMEM medium supplemented with 10% FBS and 1% penicillin-streptomycin. For monolayer cytotoxicity experiments 3000 or 5000 cells were seeded into the each well of 96-well plate for 48 h and 24 h continuous treatment times, respectively. After overnight incubation of the plates, the cells were treated with CUR and/or DOX as free drugs or micellar formulations. CellTiter-Blue was used as the cytotoxicity evaluation method as described above.

For 3D cancer cell spheroid preparation, liquid overlay method was used. Briefly, serum free DMEM medium with 1.5% (w/v) agar was prepared and sterilized. 50 μL of the agar solution were added to the bottom of each well of the 96 well plates to prevent cell adhesion onto the well surface. Plates were allowed to cool down for 45 minutes before use. U87MG cells were trypsinized, counted and then seeded at the density of 10,000 cells/well. Plates were centrifuged for 15 min at 1,500 rcf at 24° C. Spheroid formation was continuously followed using Nikon Eclipse E400 microscope (Nikon Inc., Melville, NY) with the Spot Insight camera and Spot Advanced software (Spot Imaging, Sterling Heights, MI). When the spheroids are formed and dense after 5 days, they were treated with the formulations. Cellular viability of the spheroids was determined after 48 h treatment. After the treatment with different formulations, drug concentrations and combinations, all the media from the corresponding wells along with the spheroids were collected and placed in a centrifuge tube. Five spheroids were collected as one replicate to increase the sensitivity. The spheroids were washed two times with PBS. Following removal of the remaining PBS, AccuMax® cell detachment solution was added and tubes were incubated for 10 minutes at 37° C. on the horizontal shaker with occasional pipetting. After dispersing of the spheroids into single cells, FBS was added into the tubes. Obtained cells were centrifuged and supernatants were discarded. Complete DMEM and CellTiter-Glo reagent at 1:1 volume ratio was added into the tubes and cells were incubated for 20 minutes for complete cell lysis. Luminescence was measured using multiplate reader by transferring 100 µL of the solution into 96 well black-walled plates.

Example 5: Compositions and Methods

As described herein, the inventor has developed various compositions and methods for the treatment of cancers and associated conditions. In one embodiment, the present invention provides a method of treating cancer and/or inhibiting growth in a tumor cell in a subject, by providing a composition comprising a micelle targeted by a glut-1 receptor antibody and attached to one or more curcumin and/or dox molecules, and administering a therapeutically effective dosage to the subject. In another embodiment, the composition is administered to the subject intravenously. In another embodiment the glut-1 receptor antibody is a single chain antibody. In another embodiment, the glut-1 receptor antibody is GLUT-1_1 and/or GLUT1_2 scFV. In another embodiment, the tumor cell is an ovarian tumor. In another embodiment, the tumor cell is a brain tumor. In another embodiment, the tumor cell is A2780. In another embodiment, the tumor cell is U87MG.

In accordance with embodiments further described herein, the inventor developed and optimized cancer therapeutic compositions and methods for effective delivery and minimized toxicity. For example, in one embodiment, utilizing a single chain antibody allowed a more efficient delivery in conjunction with various embodiments herein. Also, for example, by utilizing dox attached to a targeted micelle as a lipid-based delivery vehicle, rather than liposomal dox, or just dox, for example, the inventor created a cancer treatment with significantly high penetration of tumor mass. In addition to creating high tumor mass penetration, administering a composition comprising a dox attached to a targeted micelle optimized intracellular delivery of dox within the tumor cell itself. Because dox acts as a weakly basic compound, if it enters a low pH environment, or the lysosome of a tumor cell for example, the dox can lose much of its effectiveness for inhibiting tumor cell growth. By administering dox attached to a targeted micelle, rather than administering liposomal dox for example, the inventor enabled the dox to instead enter the cytoplasm, thus optimizing intracellular delivery. Additionally, dox can have high toxicity which can thus limit its practical application in vivo and usefulness as a cancer treatment for human subjects. In contrast, the inventor administered dox attached to a targeted micelle, resulting in further optimization of its effectiveness as a cancer therapeutic.

In accordance with various embodiments further disclosed herein, the inventor also attached curcumin to a targeted micelle. Due to its non-soluble properties, if administered directly, curcumin must be administered at high concentrations to be effective inhibiting tumor growth. However, at those same high concentrations, curcumin results in high toxicity, thus making it an impractical and ineffective cancer treatment in vivo, and particularly difficult for use in human patients. In accordance with an embodiment herein, by attaching curcumin to a targeted micelle, treatment can be administered at a significantly lower dosage, thus reducing toxicity while effectively inhibiting tumor growth.

As compared to the liposomal forms of both doxorubicin and curcumin, a micellar preparation is of significantly smaller molecular size (10-20 nm vs. 80-150 nm liposomes) resulting in improved tumor mass penetration from the vascular bed, thus creating a more effective cancer therapeutic. Additionally, in accordance with an embodiment herein, the addition of the Glut-1 Ab to the micelle greatly increased its therapeutic efficacy over the un-targeted micelle preparations through improved intracellular delivery of its contents. Glut-1 presents an attractive extracellular target since it is one of the main glucose transporters involved in tumor glucose uptake. Solid tumors can take up glucose at much higher rates than do normal cells. Glycolysis represents a main source of energy and carbon building blocks for growing tumors. Thus, in accordance with an embodiment herein, a micelle construct with a Glut-1 Ab is an effective cancer therapeutic, as glut-1 overexpression will persist even in the face of tumor phenotypic evolution, and it will be difficult for tumors to mutate away from glut-1 overexpression and still retain their high growth potential. In regard to using glut-1 as the tumor targeting entity, by binding to the tumor membrane-overexpressed glut-1, various embodiments of therapeutic micelles described herein get endocytosed into the cytoplasm rather than the low-pH lysosome, thereby increasing the therapeutic efficacy of doxorubicin (which has much lower activity at low pH).

Since the tumor lines used in these experiments were doxorubicin-resistant, it was critical that curcumin delivery occurred contemporaneously with doxorubicin exposure in order for it to exert its tumoricidal effect. As NFκB overexpression and its attendant apoptosis- and chemotherapy-resistance are present in advanced cancers, the inventor designed various embodiments herein to include an NFκB inhibitor (for example, curcumin) in order to unlock the cidal effect of doxorubicin. In one embodiment, the present invention is a tumor-targeted micelle containing a tumor-cidal agent coupled with an apoptosis inhibitor with significant in vivo tumor inhibitory effect and clear applicability to human cancer therapeutics.

Example 6: Efficacy on Chemo-Resistant Ovarian Carcinoma Cells (A2780/Adr)

In one embodiment, the inventor has demonstrated the efficacy of the compounds and micelles disclosed herein in studies on Doxorubicin-resistant ovarian carcinoma cells. At 20/0.4 uM CUR/DOX concentration, the enhancing effect of the Glut1 antibody targeting is clearly visible with reduced tumor cell viability.

As illustrated in FIG. 1, the efficacy of CUR40/DOX0.8 micelles on Doxorubicin-resistant ovarian carcinoma cell lines, A2780/Adr, after 48 hours of continuous contact has been determined. The columns show the cell viability at CUR/DOX concentrations 80/1.6, 40/0.8, 20/0.4, 10/0.2, 5/0.1, 2.5/0.05, 1.25/0.025. Experimental data comparing the cell viability of EmptyMicelles, G1_1-EmptyMicelles, G1_2-EmptyMicelles, CUR40/DOX0.8 Micelles, G1_1-CUR40/DOX0.8 Micelles, and G1_2-CUR40/DOX0.8 micelles is shown.

Figure 2:
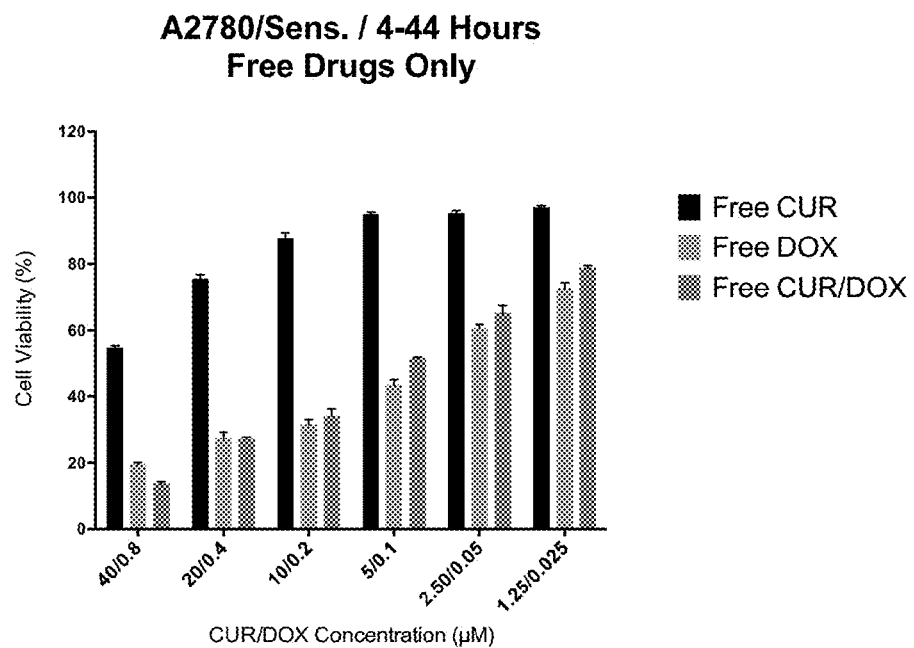
FIG. 2 depicts, in accordance with the embodiments herein, the efficacy of free CUR, free DOX, and free CUR/DOX on Doxorubicin-sensitive ovarian carcinoma cell lines, A2780/Sens, after 4-44 hours of contact. Experimental data compares the cell viability of free CUR, free DOX, and free CUR/DOX at CUR/DOX (uM) concentrations: 40/0.8, 20/0.4, 10/0.2, 5/0.1, 2.5/0.05, and 1.25/0.025.

As illustrated in FIG. 2, the efficacy of free CUR, free DOX, and free CUR/DOX on Doxorubicin-sensitive ovarian carcinoma cell lines, A2780/Sens, after 4-44 hours of contact has been determined. Experimental data comparing the cell viability of free CUR, free DOX, and free CUR/DOX at CUR/DOX (uM) concentrations: 40/0.8, 20/0.4, 10/0.2, 5/0.1, 2.5/0.05, and 1.25/0.025 is shown.

Figure 3:
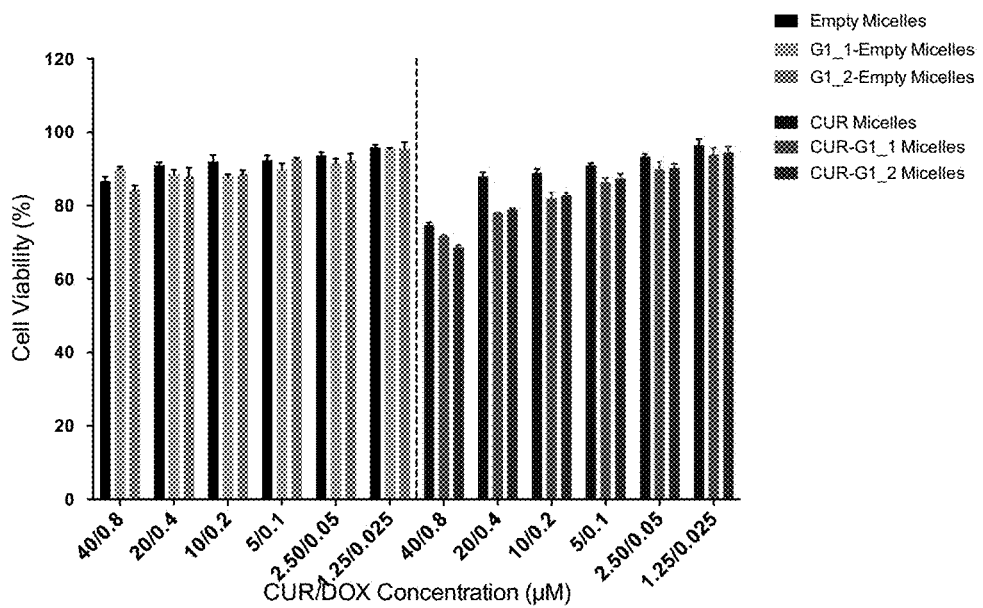
FIG. 3 depicts, in accordance with the embodiments herein, the efficacy of Empty and CUR-only micelles on Doxorubicin-sensitive ovarian carcinoma cell lines, A2780/Sens, after 4-44 hours of contact. The data compares the cell viability (%) of EmptyMicelles, G1_1-EmptyMicelles, G1_2-EmptyMicelles, CUR Micelles, CUR-G1_1 Micelles and CUR-G1_2 Micelles at CUR/DOX (uM) concentrations 40/0.8, 20/0.4, 10/0.2, 5/0.1, 2.5/0.05, and 1.25/0.025.

As illustrated in FIG. 3, the efficacy of empty and CUR-only micelles on Doxorubicin-sensitive ovarian carcinoma cell lines, A2780/Sens, after 4-44 hours of contact has been determined. The data comparing the cell viability (%) of EmptyMicelles, G1_1-EmptyMicelles, G1_2-EmptyMicelles, CUR Micelles, CUR-G1_1 Micelles and CUR-G1_2 Micelles at CUR/DOX (uM) concentrations 40/0.8, 20/0.4, 10/0.2, 5/0.1, 2.5/0.05, and 1.25/0.025 is shown.

Figure 4:
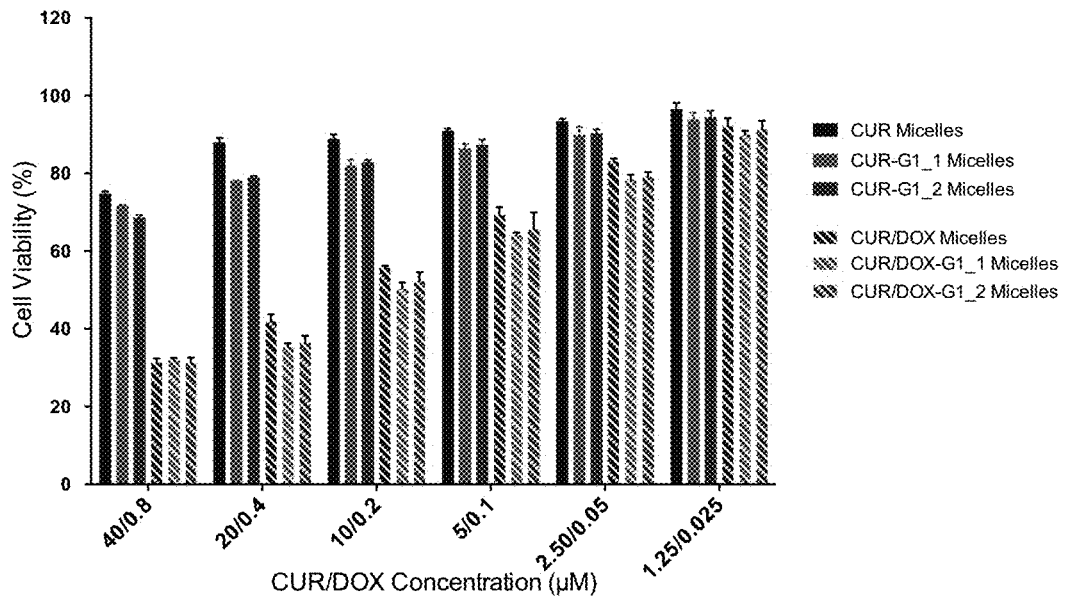
FIG. 4 depicts, in accordance with the embodiments herein, the efficacy of CUR and CUR/DOX micelles on Doxorubicin-sensitive ovarian carcinoma cell lines, A2780/Sens, after 4-44 hours of contact. The columns show the cell viability at CUR/DOX concentrations 40/0.8, 20/0.4, 10/0.2, 5/0.1, 2.5/0.05, and 1.25/0.025. Experimental data compares the cell viability of CUR Micelles, CUR-G1_1 Micelles, CUR-G1 Micelles, CUR/DOX Micelles, CUR/DOX-G1_1 Micelles, and CUR/DOX-G1_2 Micelles.

As illustrated in FIG. 4, the efficacy of CUR and CUR/DOX micelles on Doxorubicin-sensitive ovarian carcinoma cell lines, A2780/Sens, after 4-44 hours of contact has been determined. The columns show the cell viability at CUR/DOX concentrations 40/0.8, 20/0.4, 10/0.2, 5/0.1, 2.5/0.05, and 1.25/0.025. Experimental data comparing the cell viability of CUR Micelles, CUR-G1_1 Micelles, CUR-G1 Micelles, CUR/DOX Micelles, CUR/DOX-G1_1 Micelles, and CUR/DOX-G1_2 Micelles is shown.

Figure 5:
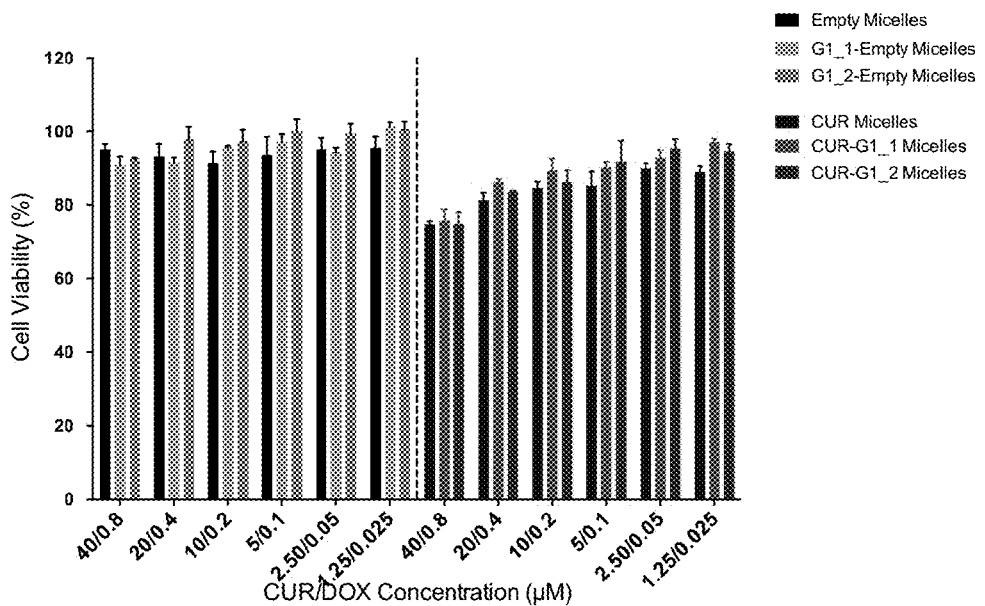
FIG. 5 depicts, in accordance with the embodiments herein, the efficacy of empty and CUR-only micelles on Doxorubicin-resistant ovarian carcinoma cell lines, A2780/Adr after 4-44 hours of contact. The columns show the cell viability at CUR/DOX (uM) concentrations 40/0.8, 20/0.4, 10/0.2, 5/0.1, 2.5/0.05, and 1.25/0.025. Experimental data compares the cell viability of Empty Micelles, G1_1-Empty Micelles, G1_2-Empty Micelles, CUR Micelles, CUR-G1_1 Micelles, and CUR-G1_2 Micelles.

As illustrated in FIG. 5, the efficacy of empty and CUR-only micelles on Doxorubicin-resistant ovarian carcinoma cell lines, A2780/Adr after 4-44 hours of contact has been determined. The columns show the cell viability at CUR/DOX (uM) concentrations 40/0.8, 20/0.4, 10/0.2, 5/0.1, 2.5/0.05, and 1.25/0.025. Experimental data comparing the cell viability of Empty Micelles, G1_1-Empty Micelles, G1_2-Empty Micelles, CUR Micelles, CUR-G1_1 Micelles, and CUR-G1_2 Micelles is shown.

Figure 6:
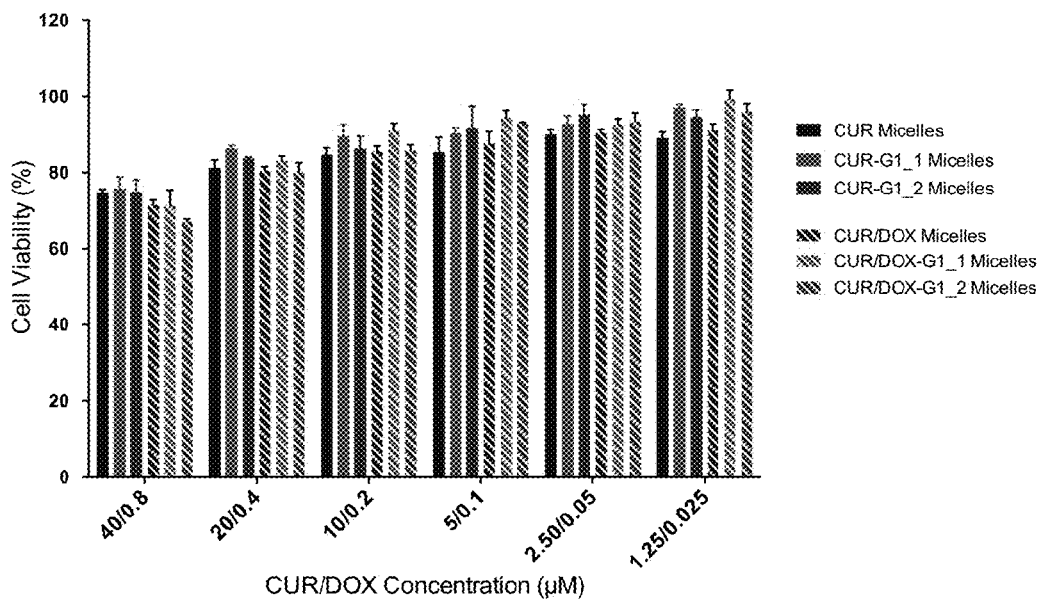
FIG. 6 depicts, in accordance with the embodiments herein, the efficacy of CUR and CUR/DOX micelles on Doxorubicin-resistant ovarian carcinoma cell lines, A2780/Adr after 4-44 hours of contact. The columns show the cell viability at CUR/DOX (uM) concentrations 40/0.8, 20/0.4, 10/0.2, 5/0.1, 2.5/0.05, and 1.25/0.025. Experimental data compares the cell viability of CUR Micelles, CUR-G1_1 Micelles, CUR-G1_2 Micelles, CUR/DOX Micelles, CUR/DOX-G1_1 Micelles, and CUR/DOX-G1_2 Micelles.

As illustrated in FIG. 6, the efficacy of CUR and CUR/DOX micelles on Doxorubicin-resistant ovarian carcinoma cell lines, A2780/Adr after 4-44 hours of contact has been determined. The columns show the cell viability at CUR/DOX (uM) concentrations 40/0.8, 20/0.4, 10/0.2, 5/0.1, 2.5/0.05, and 1.25/0.025. Experimental data comparing the cell viability of CUR Micelles, CUR-G1_1 Micelles, CUR-G1_2 Micelles, CUR/DOX Micelles, CUR/DOX-G1_1 Micelles, and CUR/DOX-G1_2 Micelles is shown.

Figure 7:
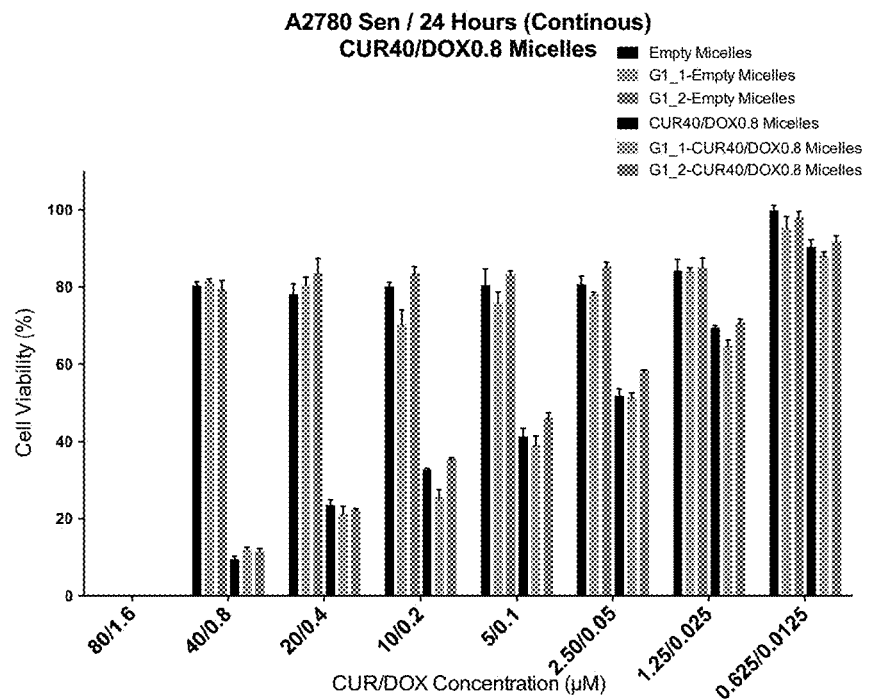
FIG. 7 depicts, in accordance with the embodiments herein, the efficacy of CUR40/DOX0.8 micelles on Doxorubicin-sensitive ovarian carcinoma cell lines, A2780/Sen after 24 hours of continuous contact. The columns show the cell viability at CUR/DOX (uM) concentrations 80/1.6, 40/0.8, 20/0.4, 10/0.2, 5/0.1, 2.5/0.05, 1.25/0.025, and 0.625/0.0125. Experimental data compares the cell viability of Empty Micelles, G1_1-Empty Micelles, G1_2-Empty Micelles, CUR40/DOX0.8 Micelles, G1_1-CUR40/DOX0.8 Micelles, and G1_2-CUR40/DOX0.8 Micelles.

As illustrated in FIG. 7, the efficacy of CUR40/DOX0.8 micelles on Doxorubicin-sensitive ovarian carcinoma cell lines, A2780/Sen after 24 hours of continuous contact has been determined. The columns show the cell viability at CUR/DOX (uM) concentrations 80/1.6, 40/0.8, 20/0.4, 10/0.2, 5/0.1, 2.5/0.05, 1.25/0.025, and 0.625/0.0125. Experimental data comparing the cell viability of Empty Micelles, G1_1-Empty Micelles, G1_2-Empty Micelles, CUR40/DOX0.8 Micelles, G1_1-CUR40/DOX0.8 Micelles, and G1_2-CUR40/DOX0.8 Micelles is shown.

Figure 8:
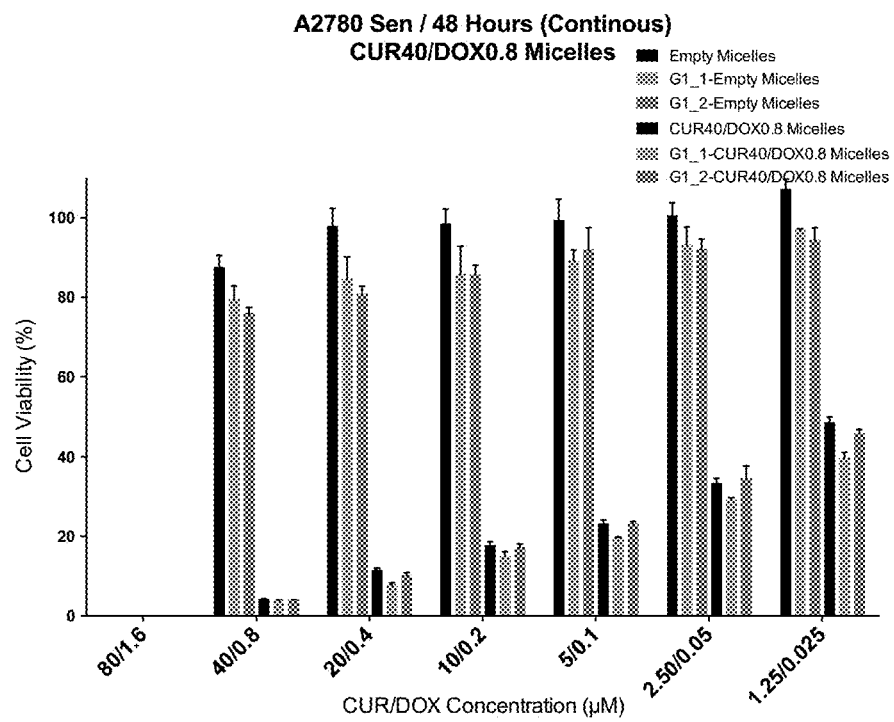
FIG. 8 depicts, in accordance with the embodiments herein, the efficacy of CUR40/DOX0.8 micelles on Doxorubicin-sensitive ovarian carcinoma cell lines, A2780/Sen, after 48 hours of continuous contact. The columns show the cell viability at CUR/DOX (uM) concentrations 80/1.6, 40/0.8, 20/0.4, 10/0.2, 5/0.1, 2.5/0.05, and 1.25/0.025. Experimental data compares the cell viability of Empty Micelles, G1_1-Empty Micelles, G1_2-Empty Micelles, CUR40/DOX0.8 Micelles, G1_1-CUR40/DOX0.8 Micelles, and G1_2-CUR40/DOX0.8 Micelles.

As illustrated in FIG. 8, the efficacy of CUR40/DOX0.8 micelles on Doxorubicin-sensitive ovarian carcinoma cell lines, A2780/Sen, after 48 hours of continuous contact has been determined. The columns show the cell viability at CUR/DOX (uM) concentrations 80/1.6, 40/0.8, 20/0.4, 10/0.2, 5/0.1, 2.5/0.05, and 1.25/0.025. Experimental data comparing the cell viability of Empty Micelles, G1_1-Empty Micelles, G1_2-Empty Micelles, CUR40/DOX0.8 Micelles, G1_1-CUR40/DOX0.8 Micelles, and G1_2-CUR40/DOX0.8 Micelles is shown.

Figure 9:
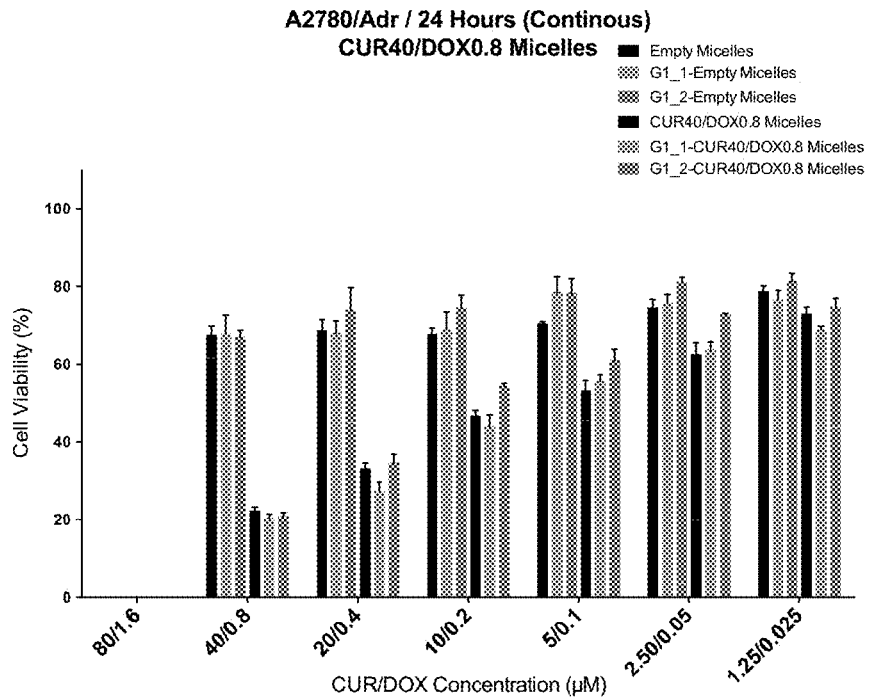
FIG. 9 depicts, in accordance with the embodiments herein, the efficacy of CUR40/DOX0.8 micelles on Doxorubicin-resistant ovarian carcinoma cell lines, A2780/Adr after 24 hours of continuous contact. The columns show the cell viability at CUR/DOX (uM) concentrations 80/1.6, 40/0.8, 20/0.4, 10/0.2, 5/0.1, 2.5/0.05, and 1.25/0.025. Experimental data compares the cell viability of Empty Micelles, G1_1-Empty Micelles, G1_2-Empty Micelles, CUR40/DOX0.8 Micelles, G1_1-CUR40/DOX0.8 Micelles, and G1_2-CUR40/DOX0.8 Micelles.

As illustrated in FIG. 9, the efficacy of CUR40/DOX0.8 micelles on Doxorubicin-resistant ovarian carcinoma cell lines, A2780/Adr after 24 hours of continuous contact has been determined. The columns show the cell viability at CUR/DOX (uM) concentrations 80/1.6, 40/0.8, 20/0.4, 10/0.2, 5/0.1, 2.5/0.05, and 1.25/0.025. Experimental data comparing the cell viability of Empty Micelles, G1_1-Empty Micelles, G1_2-Empty Micelles, CUR40/DOX0.8 Micelles, G1_1-CUR40/DOX0.8 Micelles, and G1_2-CUR40/DOX0.8 Micelles is shown.

Figure 10:
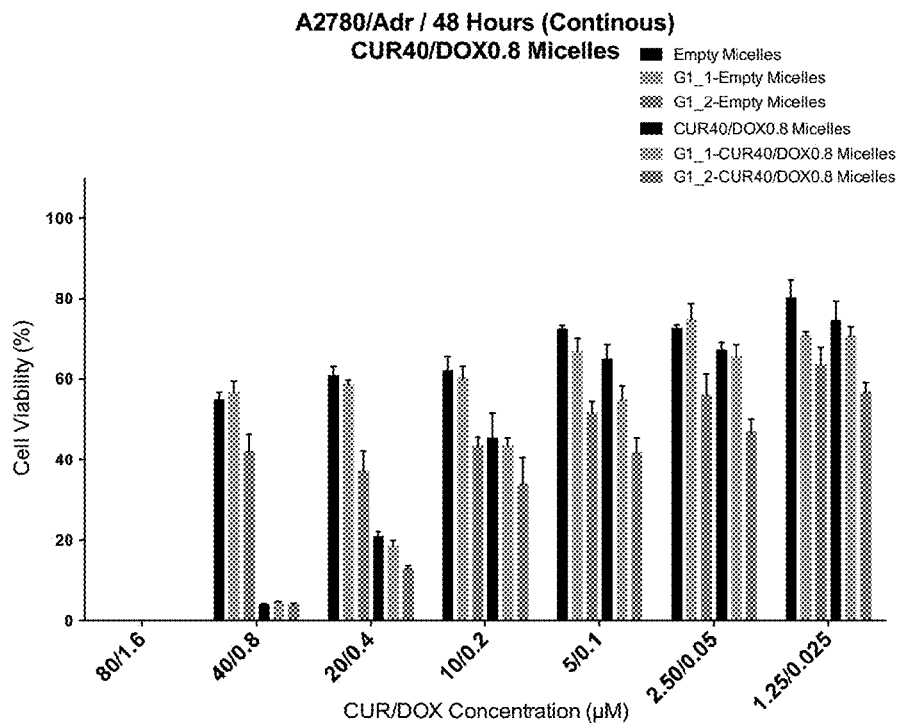
FIG. 10 depicts, in accordance with the embodiments herein, the efficacy of CUR40/DOX0.8 micelles on Doxorubicin-resistant ovarian carcinoma cell lines, A2780/Adr, after 48 hours of continuous contact. The columns show the cell viability at CUR/DOX (uM) concentrations 80/1.6, 40/0.8, 20/0.4, 10/0.2, 5/0.1, 2.5/0.05, and 1.25/0.025. Experimental data compares the cell viability of Empty Micelles, G1_1-Empty Micelles, G1_2-Empty Micelles, CUR40/DOX0.8 Micelles, G1_1-CUR40/DOX0.8 Micelles, and G1_2-CUR40/DOX0.8 Micelles.

As illustrated in FIG. 10, the efficacy of CUR40/DOX0.8 micelles on Doxorubicin resistant ovarian carcinoma cell lines, A2780/Adr, after 48 hours of continuous contact has been determined. The columns show the cell viability at CUR/DOX (uM) concentrations 80/1.6, 40/0.8, 20/0.4, 10/0.2, 5/0.1, 2.5/0.05, and 1.25/0.025. Experimental data comparing the cell viability of Empty Micelles, G1_1-Empty Micelles, G1_2-Empty Micelles, CUR40/DOX0.8 Micelles, G1_1-CUR40/DOX0.8 Micelles, and G1_2-CUR40/DOX0.8 Micelles is shown.

Example 7: Efficacy on Colon Cancer Cell Lines

In one embodiment, the inventor has demonstrated the efficacy of the compounds and micelles disclosed herein on human colon carcinoma cell line HCT-116.

Figure 11:
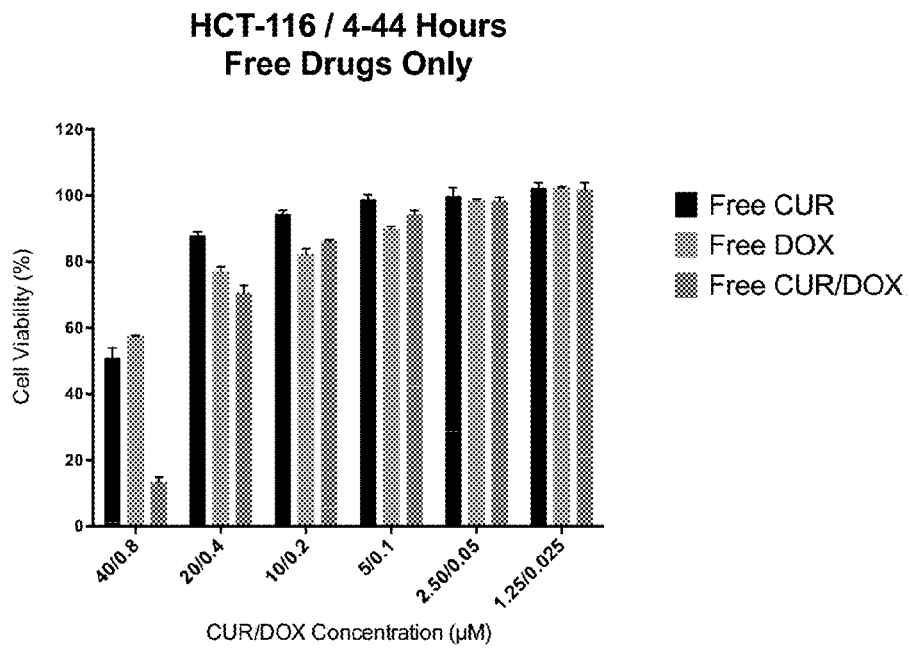
FIG. 11 depicts, in accordance with the embodiments herein, the efficacy of free CUR, free DOX, and free CUR/DOX on HCT-116 cells after 4-44 hours of contact. The columns illustrate the cell viability (%) at CUR/DOX (uM) concentrations: 40/0.8, 20/0.4, 10/0.2, 5/0.1, 2.5/0.05, and 1.25/0.025.

As illustrated in FIG. 11, the efficacy of free CUR, free DOX, and free CUR/DOX on HCT-116 cells after 4-44 hours of contact has been determined. The columns illustrate the cell viability (%) at CUR/DOX (uM) concentrations: 40/0.8, 20/0.4, 10/0.2, 5/0.1, 2.5/0.05, and 1.25/0.025.

Figure 12:
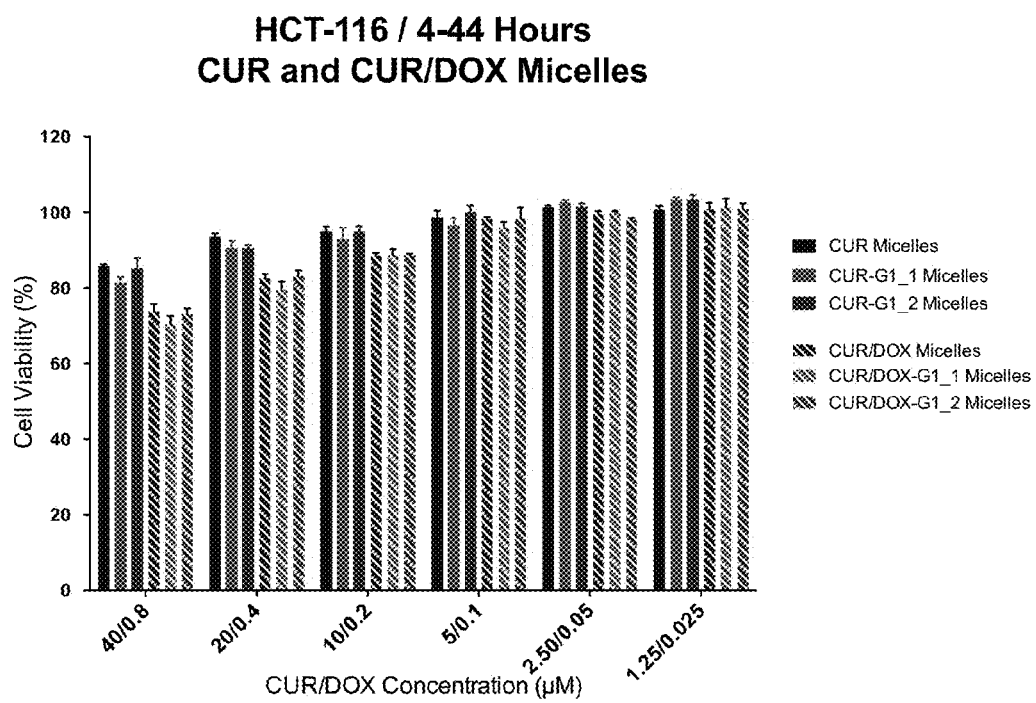
FIG. 12 depicts, in accordance with the embodiments herein, the efficacy of CUR and CUR/DOX micelles on HCT-116 cells after 4-44 hours of contact. The columns show the cell viability at CUR/DOX (uM) concentrations 40/0.8, 20/0.4, 10/0.2, 5/0.1, 2.5/0.05, and 1.25/0.025. Experimental data compares the cell viability of CUR Micelles, CUR-G1_1 Micelles, CUR-G1_2 Micelles, CUR/DOX Micelles, CUR/DOX-G1_1 Micelles, and CUR/DOX-G1_2 Micelles.

As illustrated in FIG. 12, the efficacy of CUR and CUR/DOX micelles on HCT-116 cells after 4-44 hours of contact has been determined. The columns show the cell viability at CUR/DOX (uM) concentrations 40/0.8, 20/0.4, 10/0.2, 5/0.1, 2.5/0.05, and 1.25/0.025. Experimental data comparing the cell viability of CUR Micelles, CUR-G1_1 Micelles, CUR-G1_2 Micelles, CUR/DOX Micelles, CUR/DOX-G1_1 Micelles, and CUR/DOX-G1_2 Micelles is shown.

Figure 13:
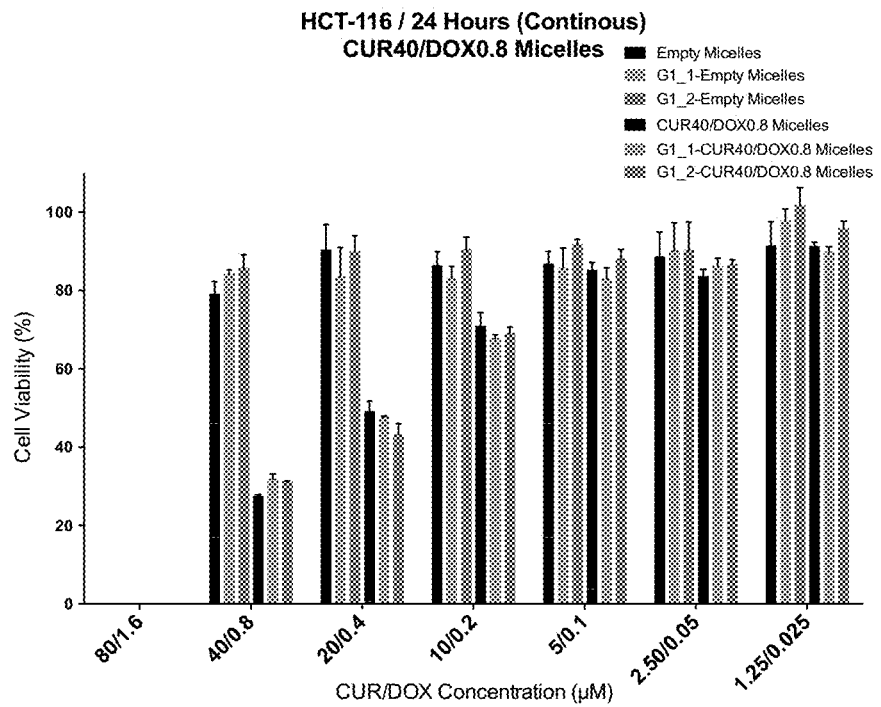
FIG. 13 depicts, in accordance with the embodiments herein, the efficacy of CUR40/DOX0.8 micelles HCT-116 cells after 24 hours of continuous contact. The columns show the cell viability at CUR/DOX (uM) concentrations 80/1.6, 40/0.8, 20/0.4, 10/0.2, 5/0.1, 2.5/0.05, and 1.25/0.025. Experimental data compares the cell viability (%) of Empty Micelles, G1_1-Empty Micelles, G1_2-Empty Micelles, CUR40/DOX0.8 Micelles, G1_1-CUR40/DOX0.8 Micelles, and G1_2-CUR40/DOX0.8 Micelles.

As illustrated in FIG. 13, the efficacy of CUR40/DOX0.8 micelles HCT-116 cells after 24 hours of continuous contact has been determined. The columns show the cell viability at CUR/DOX (uM) concentrations 80/1.6, 40/0.8, 20/0.4, 10/0.2, 5/0.1, 2.5/0.05, and 1.25/0.025. Experimental data comparing the cell viability (%) of Empty Micelles, G1_1-Empty Micelles, G1_2-Empty Micelles, CUR40/DOX0.8 Micelles, G1_1-CUR40/DOX0.8 Micelles, and G1_2-CUR40/DOX0.8 Micelles is shown.

Figure 14:
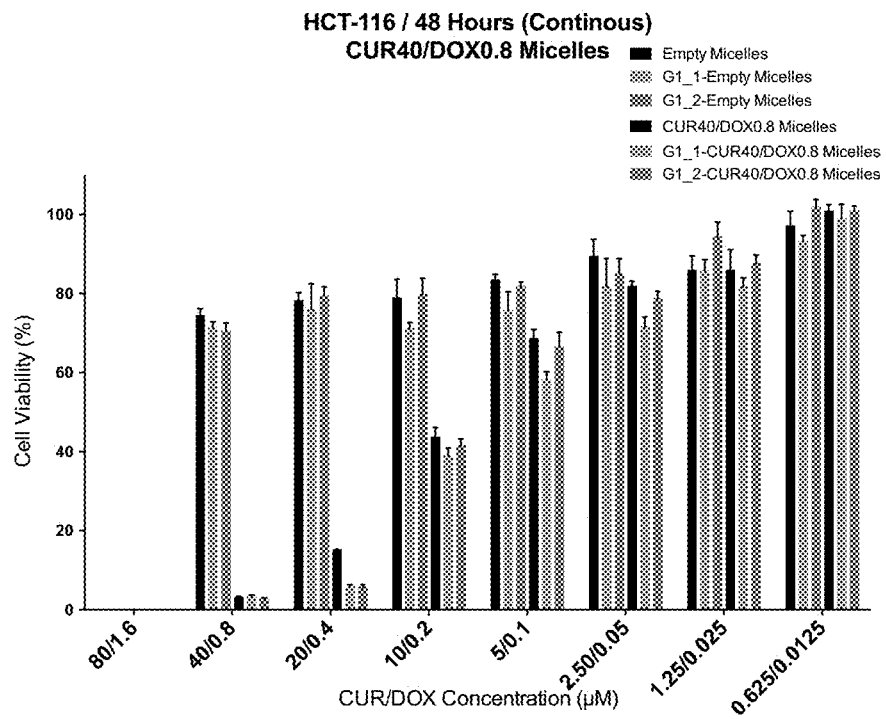
FIG. 14 depicts, in accordance with the embodiments herein, the efficacy of CUR40/DOX0.8 micelles on HCT-116 cells after 48 hours of continuous contact. The columns show the cell viability at CUR/DOX (uM) concentrations 80/1.6, 40/0.8, 20/0.4, 10/0.2, 5/0.1, 2.5/0.05, and 1.25/0.025. Experimental data compares the cell viability (%) of Empty Micelles, G1_1-Empty Micelles, G1_2-Empty Micelles, CUR40/DOX0.8 Micelles, G1_1-CUR40/DOX0.8 Micelles, and G1_2-CUR40/DOX0.8 Micelles.

As illustrated in FIG. 14, the efficacy of CUR40/DOX0.8 micelles on HCT-116 cells after 48 hours of continuous contact has been determined. The columns show the cell viability at CUR/DOX (uM) concentrations 80/1.6, 40/0.8, 20/0.4, 10/0.2, 5/0.1, 2.5/0.05, and 1.25/0.025. Experimental data comparing the cell viability (%) of Empty Micelles, G1_1-Empty Micelles, G1_2-Empty Micelles, CUR40/DOX0.8 Micelles, G1_1-CUR40/DOX0.8 Micelles, and G1_2-CUR40/DOX0.8 Micelles is shown.

Example 8: Efficacy on Brain Cancer Cell Line

In one embodiment, the efficacy of the compounds and micelles disclosed herein has been demonstrated on human primary glioblastoma cell line U87MG. GLUT 1_1 and GLUT 1_2 scFv are two anti-Glut1 scFv's that was produced. The experiments were performed with U87MG monolayer treated with micelles. So far, this cell line was more responsive line to GLUT 1_1 and GLUT 1_2 scFv. 48 hours of contact was too much for this cell line because the cytotoxicity effect was saturated with drugs. However for 24 hours, the row and column effects were significant means that there was a dose response and also the antibody targeting effect. Significant difference corresponded to difference between non-targeted micelles to GLUT 1_1 or GLUT 1_2 targeted micelles, two-way ANOVA, $P<0.05$. In accordance with various embodiments, administration to U87MGs responded well to GLUT 1_2.

Figure 15:
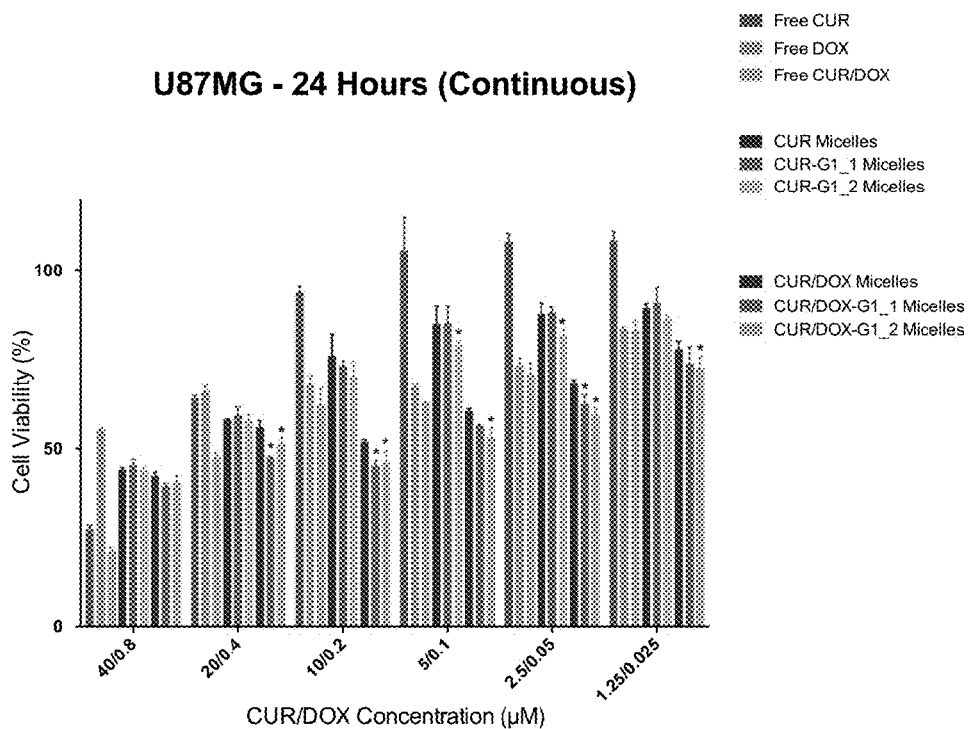
FIG. 15 depicts, in accordance with the embodiments herein, the efficacy of free drugs and micelles on U87MG cells after 24 hours of continuous contact. The columns show the cell viability at CUR/DOX (uM) concentrations 40/0.8, 20/0.4, 10/0.2, 5/0.1, 2.5/0.05, and 1.25/0.025. Experimental data compares the cell viability (%) of free CUR, free DOX, free CUR/DOX, CUR Micelles, CUR-G1_1 Micelles, CUR-G1_2 Micelles, CUR/DOX Micelles, CUR/DOX-G1_1 Micelles, and CUR/DOX-G1_2 Micelles.

As illustrated in FIG. 15, the efficacy of free drugs and micelles on U87MG cells after 24 hours of continuous contact has been determined. The columns show the cell viability at CUR/DOX (uM) concentrations 40/0.8, 20/0.4, 10/0.2, 5/0.1, 2.5/0.05, and 1.25/0.025. Experimental data comparing the cell viability (%) of free CUR, free DOX, free CUR/DOX, CUR Micelles, CUR-G1_1 Micelles, CUR-G1_2 Micelles, CUR/DOX Micelles, CUR/DOX-G1_1 Micelles, and CUR/DOX-G1_2 Micelles is shown.

Figure 16:
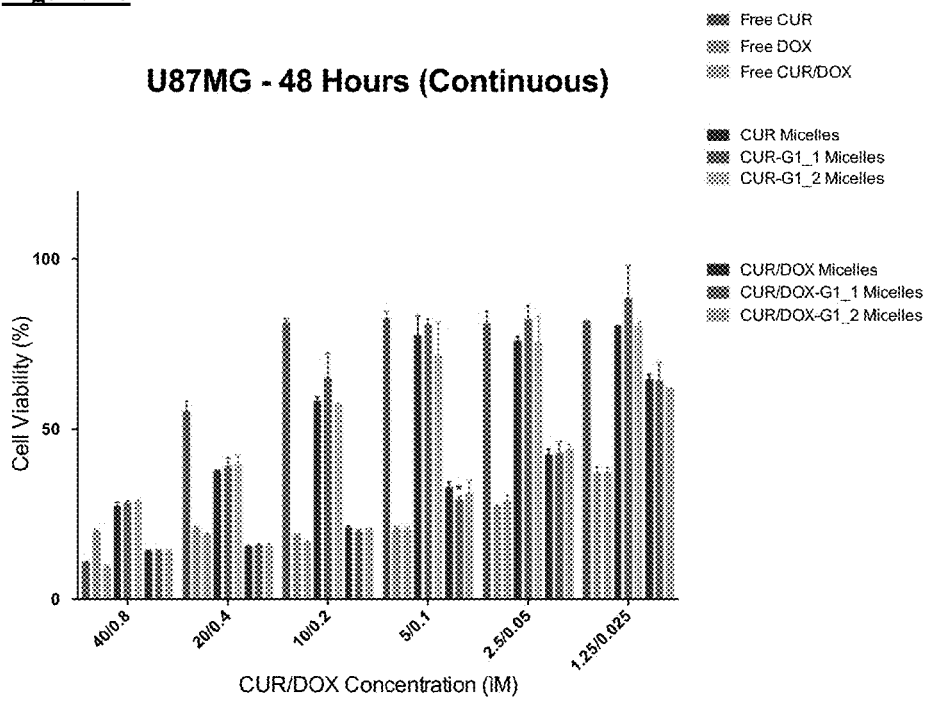
FIG. 16 depicts, in accordance with the embodiments herein, the efficacy of free drugs and micelles on U87MG cells after 48 hours of continuous contact. The columns show the cell viability (%) at CUR/DOX (uM) concentrations 40/0.8, 20/0.4, 10/0.2, 5/0.1, 2.5/0.05, and 1.25/0.025. Experimental data compares the cell viability of free CUR, free DOX, free CUR/DOX, CUR Micelles, CUR-G1_1 Micelles, CUR-G1_2 Micelles, CUR/DOX Micelles, CUR/DOX-G1_1 Micelles, and CUR/DOX-G1_2 Micelles.

As illustrated in FIG. 16, the efficacy of free drugs and micelles on U87MG cells after 48 hours of continuous contact has been determined. The columns show the cell viability (%) at CUR/DOX (uM) concentrations 40/0.8, 20/0.4, 10/0.2, 5/0.1, 2.5/0.05, and 1.25/0.025. Experimental data comparing the cell viability of free CUR, free DOX, free CUR/DOX, CUR Micelles, CUR-G1_1 Micelles, CUR-G1_2 Micelles, CUR/DOX Micelles, CUR/DOX-G1_1 Micelles, and CUR/DOX-G1_2 Micelles is shown.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A pharmaceutical composition comprising:
 a micelle construct comprising
   1,2-distearoyl-sn-glycero-3-phosphoethanolamine-N-[methoxy (polyethylene glycol)-2000] (PEG$_{2000}$-PE);
   curcumin or a pharmaceutical equivalent, analog, derivative, or salt thereof; and
   a chemotherapy agent;
 wherein the average diameter of the micelle construct is less than 30 nm.

2. The composition of claim 1, wherein the curcumin is a compound having the structure of formula 1:

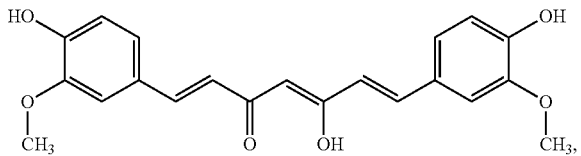

or compound having the structure of formula 2:

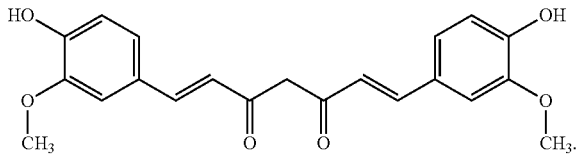 [SMILES: COc1cc(/C=C/C(=O)CC(=O)/C=C/c2ccc(O)c(OC)c2)ccc1O]

3. The composition of claim 1, wherein the chemotherapy agent is doxoruhicin or a pharmaceutical equivalent, analog, derivative, and/or salt thereof.

4. The composition of claim 1, wherein the average diameter of the micelle construct is between 10 nm and 20 nm.

5. The composition of claim 1, further comprising a pharmaceutically acceptable carrier.

6. The composition of claim 1, wherein the average diameter of the micelle construct is less than 20 nm.

7. A method of treating cancer in a subject, comprising administering a therapeutically effective dosage of the composition of claim 1 to the subject.

8. The method of claim 7, wherein the subject is a human.

9. The method of claim 7, wherein the cancer is colon cancer.

10. The method of claim 7, wherein the cancer is breast cancer.

11. The method of claim 7, wherein the cancer is brain cancer.

12. The method of claim 7, wherein the cancer is a chemotherapy-resistant cell.

13. A method of inhibiting cell growth of a tumorcell, comprising:
 providing the composition of claim 1; and
 inhibiting cell growth by administering a therapeutically effective dosage to the tumor cell.

14. The method of claim 13, wherein the tumor cell is a breast cancer cell.

15. The method of claim 13, wherein the tumor cell is a colon cancer cell.

16. The method of claim 13, wherein the tumor cell is a brain cancer cell.

* * * * *